United States Patent
Steinhagen et al.

(10) Patent No.: US 7,910,602 B2
(45) Date of Patent: Mar. 22, 2011

(54) PYRAZOLOPYRIDINE DERIVATIVES AS INHIBITORS OF β-ADRENERGIC RECEPTOR KINASE 1

(75) Inventors: Henning Steinhagen, Frankfurt (DE); Jochen Huber, Frankfurt (DE); Kurt Ritter, Frankfurt (DE); Bernard Pirard, Hegenheim (FR); Kirsten Bjergarde, Tucson, AZ (US); Marcel Patek, Tucson, AZ (US); Martin Smrcina, Tucson, AZ (US); Linli Wei, Bridgewater, NJ (US)

(73) Assignee: Sanofi-Aventis, Paris (FR)

( * ) Notice: Subject to any disclaimer, the term of this patent is extended or adjusted under 35 U.S.C. 154(b) by 487 days.

(21) Appl. No.: 11/961,282

(22) Filed: Dec. 20, 2007

(65) Prior Publication Data

US 2008/0227777 A1    Sep. 18, 2008

Related U.S. Application Data

(63) Continuation of application No. PCT/EP2006/005649, filed on Jun. 13, 2006.

(30) Foreign Application Priority Data

Jun. 27, 2005  (EP) .................................... 05013774

(51) Int. Cl.
*A61K 31/44* (2006.01)
*A01N 43/42* (2006.01)
*C07D 471/02* (2006.01)
*C07D 491/02* (2006.01)
*C07D 498/02* (2006.01)
*C07D 513/02* (2006.01)

(52) U.S. Cl. ........................ 514/303; 546/120
(58) Field of Classification Search .................. 546/120; 544/127; 514/234.2, 258.1
See application file for complete search history.

(56) References Cited

FOREIGN PATENT DOCUMENTS

| WO | 99-30710 | 6/1999 |
|---|---|---|
| WO | WO 03-068773 | 8/2003 |
| WO | WO 2004-014910 | 2/2004 |
| WO | WO 2004-076450 | 9/2004 |

OTHER PUBLICATIONS

Tomaszewski et al., Hypertension, (Nov. 2004) vol. 44, No. 5, pp. 689-694.*
Lynch, Pyrazolo[3,4-b]pyridines: syntheses, eractions, and nuclear magnetic resonance spectra, Can. J. of Chem.; 1988; 66(3); p. 426.

* cited by examiner

*Primary Examiner* — D. Margaret Seaman
*Assistant Examiner* — Niloofar Rahmani
(74) *Attorney, Agent, or Firm* — Serena Farquharson-Torres; Scully, Scott, Murphy and Presser, P.C.

(57) ABSTRACT

The invention relates to 6-amido substituted pyrazolopyridine derivatives of the formula (I)

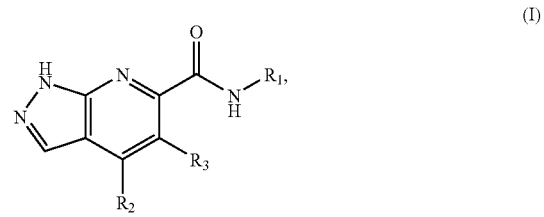

useful as inhibitors of beta-adrenergic receptor kinase 1 (βARK-1), compositions containing such compounds and their use for the treatment and prevention of chronic heart failure, hypertension, myocardial ischemia and hepatitis C virus (HCV) infections, and for the prevention of opiate addiction.

14 Claims, No Drawings

PYRAZOLOPYRIDINE DERIVATIVES AS INHIBITORS OF β-ADRENERGIC RECEPTOR KINASE 1

The sympathetic nervous system that is a critical regulator of cardiac function has been implicated in the inability of the failing heart to respond to stress or injury. In response to stress catecholamines (i.e. the sympathetic neurotransmitter norepinephrine and the adrenal hormon epinephrine) bind to myocardial adrenergic receptors (ARs). These receptors, which include β1 and β2 ARs modulate cardiac function by coupling to and activating G proteins and thus belong to the large superfamily of G protein coupled receptors (GPCRs). Agonist binding to a βAR generates a conformational change to the receptor. This conformational change permits the βAR to interact with a membrane-bound G-protein. The interaction results in the dissociation of the G-protein heterotrimer into two components, namely the Gα- and Gβγ subunits. Either of these two subunits can modulate cytosolic effector proteins that in turn may regulate production of intracellular messenger molecules. In the case of catecholamine-activated myocardial βAR, a specific G-protein, Gs, stimulates adenylyl cyclase to produce cAMP within the cell, which increases cardiac chronotropy and inotropy (Petrofski and Koch, J. Mol. Cell. Cardiol. 2003, 35, 1167-1174).

Homologous desensitization of βARs occurs via a family of serine/threonine kinases known as G-protein coupled receptor kinases (GRKs). Seven GRK family members have been identified to date. Two (GRK1 or rhodopsin kinase and GRK7) are localized primarily in the retina, whereas the remaining five (GRK2-7) are ubiquitously expressed in several tissues including the heart. GRKs have a tridomain structure with a central catalytic domain, flanked by amino-terminal (NT) and carboxy-terminal (CT) domains that contain specific regulatory sites (Iaccarino and Koch, Assay and Drug Develop. Technol. 2003, 1(2), 347-355). An interaction between the Gβγ subunit and the CT of the cytosolic GRK results in translocation of GRK to the membrane, where it can phosphorylate the activated receptor. Gβγ binding takes place with an approximate 100 amino acid stretch that is part part of the pleckstrin homology (PH) domain found in the CT of GRK2. Desensitization in the face of persistent agonist presence is termed homologous desensitization and requires not only a GRK but also an additional protein, β-arrestin. β-arrestins sterically prevent Gs-coupling to the catecholamine bound βAR (Petrofski and Koch, J. Mol. Cell. Cardiol. 2003, 35, 1167-1174).

Desensitization may be an adaptive response to GPCR stimulation, but can also lead to pathological loss of receptor signaling. Importantly, in the human heart failure, chronic activation of the sympathetic nervous system has adverse implications and can accelerate cardiac pathology. Constant stimulation of adrenergic receptors by catecholamines leads to selective β1AR downregulation (Bristow et al., New Engl. J. Med. 1982, 307 (4), 205-211). In end-stage human heart failure, GRK2 mRNA and protein, and activity are elevated approximately threefold and this causes dysfunctional βAR signaling and the loss of inotropic reserve in the frailing heart (Ungerer et al., Circulation 1993, 87, 454-463). Furthermore, myocardial ischemia and hypertension, both important causes in heart failure, are also correlated with elevated GRK2 levels (Petrofski and Koch, J. Mol. Cell. Cardiol. 2003, 35, 1167-1174).

Rockman et al. (Nature 2002, 415, 206-212) have shown that GRK2 has an important role in the pathophysiology of cardiac failure. Targeted GRK2 inhibition therefore represents a therapetic approach to treatment of the failing heart.

Besides chronic heart failure GRK2 inhibitors may be of value in the treatment of hypertension since elevated GRK2 levels have been demonstrated in peripheral blood lymphocytes of a subgroup of hypertensive patients with impaired β2AR-mediated vasodilation. Because β1AR regulation in lymphocytes parallels that observed in vascular smooth muscle cells in hypertensive subjects, the GRK2 up-regulation seen in these lymphocytes is suggested to underlie the attenuation of β2AR-mediated vasodilation in the hypertensive subjects studied (Gros R et al., J. Clin. Invest. 1997, 99, 2087-2093). GRK2 inhibitors may be also be applied in the treatment of myocardial ischemia since elevated GRK2 levels could be demonstrated in rat heart muscle deprived of oxygen for prolonged periods and this up-regulation correlates temporally with diminishing responsiveness of β-adrenergic receptor stimulated cyclase activity (Ungerer et al., Circ. Res. 1996, 79, 455-460).

The finding that increased GRK2 levels could be detected in the locus coerulus of rats after chronical treatment with morphine suggests that GRK2 inhibitors can be used to prevent opiate addiction. The increased GRK2 activity may both compensate for hyperstimulation of central nervous system opioid receptors and contribute to the problem of opiate tolerance (Terwilliger et al., J. Neurochem 1994, 63, 1983-1986).

WO 2003054228 (Axxima Pharmaceuticals AG) discloses that GRK2 (among other protein kinases, metalloproteases and phosphatases) is a potential target for medical intervention against hepatitis C virus (HCV) infections.

The terms G-protein coupled receptor kinases 2 (GRK2) and β-Adrenergic Receptor Kinase 1 (βARK-1) are used synonymously.

WO 2004/076450 describes 6-heterocyclyl or phenyl substituted pyrazolopyridine derivatives useful as p38 kinase inhibitors.

WO 03/068773 describes pyrazolopyridine derivatives as GSK-3 inhibitors useful for a variety of indications wherein the 6-position is optionally substituted by $(C_3-C_8)$cycloalkyl, heterocyclyl, heteroaryl or aryl.

WO 03/045949 describes pyrazolopyridine derivatives as GSK-3 inhibitors wherein the 6-position is unsubstituted.

WO 95/34563 and EP 1149583 describes generically describes pyrazolopyridine derivatives useful as CRF antagonists wherein the 6-position is substituted by $(C_1-C_4)$ alkyl, fluoro, chloro, bromo, iodo, —$CH_2OH$, —$CH_2OCH_3$, —$O(C_1-C_3)$alkyl, —$S(C_1-C_3)$alkyl, or —$SO_2(C_1-C_3)$alkyl.

The present invention relates to compounds of the formula (I)

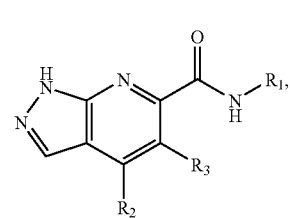

wherein
$R_1$ is H or $(C_1-C_6)$alkyl, wherein the $(C_1-C_6)$alkyl group is unsubstituted or substituted by one or more OH, halogen or $NH_2$ groups; and
$R_2$ is phenyl, $(C_3-C_{10})$cycloalkyl or a $(C_4-C_{10})$heterocyclyl group which are unsubstituted or substituted by 1, 2 or 3 residues independently selected from 1. $(C_1\text{-}C_6)$alkyl,
2. $(C_2\text{-}C_6)$alkenyl,
3. $(C_2\text{-}C_6)$alkynyl,
4. $(C_1\text{-}C_6)$alkylene-COOH,
5. $(C_1\text{-}C_6)$alkylene-C(O)O—$(C_1\text{-}C_6)$alkyl,
6. $(C_1\text{-}C_6)$alkylene-C(O)NH$_2$,
7. $(C_1\text{-}C_6)$alkylene-C(O)NH—$(C_1\text{-}C_6)$alkyl,
8. $(C_1\text{-}C_6)$alkylene-O—$(C_1\text{-}C_6)$alkyl,
9. $(C_1\text{-}C_6)$alkylene-OH,
10. $(C_1\text{-}C_6)$alkylene-NH$_2$,
11. $(C_1\text{-}C_6)$alkylene-NH—$(C_1\text{-}C_6)$alkyl,
12. $(C_1\text{-}C_6)$alkylene-N[$(C_1\text{-}C_6)$alkyl]$_2$,
13. CN,
14. COOH,
15. C(O)O—$(C_1\text{-}C_6)$alkyl,
16. C(O)NH$_2$,
17. C(O)NH—$(C_1\text{-}C_6)$alkyl,
18. C(O)N[$(C_1\text{-}C_6)$alkyl]$_2$,
19. C(O)—$(C_1\text{-}C_6)$alkyl,
20. halogen,
21. NH$_2$,
22. NH$(C_1\text{-}C_6)$alkyl,
23. N[$(C_1\text{-}C_6)$alkyl]$_2$,
24. NH—C(O)—$(C_1\text{-}C_6)$alkyl,
25. OH,
26. O—$(C_1\text{-}C_6)$alkyl,
27. O—$(C_2\text{-}C_6)$alkenyl,
28. O—$(C_2\text{-}C_6)$alkynyl,
29. O—$(C_1\text{-}C_6)$alkylene-C(O)OH,
30. O—$(C_1\text{-}C_6)$alkylene-C(O)O—$(C_1\text{-}C_6)$alkyl,
31. O—$(C_1\text{-}C_6)$alkylene-C(O)NH$_2$,
32. O—$(C_1\text{-}C_6)$alkylene-C(O)NH—$(C_1\text{-}C_6)$alkyl,
33. O—$(C_1\text{-}C_6)$alkylene-OH,
34. O—$(C_1\text{-}C_6)$alkylene-O—$(C_1\text{-}C_6)$alkyl,
35. O—$(C_1\text{-}C_6)$alkylene-NH$_2$,
36. O—$(C_1\text{-}C_6)$alkylene-NH—$(C_1\text{-}C_6)$alkyl,
37. O—C(O)—$(C_1\text{-}C_6)$alkyl,
38. S—$(C_1\text{-}C_6)$alkyl,
39. S(O)$_2$—$(C_1\text{-}C_4)$alkyl,
40. $(C_6\text{-}C_{10})$aryl,
41. $(C_4\text{-}C_{10})$heterocyclyl,
42. $(C_1\text{-}C_6)$alkylene-$(C_6\text{-}C_{10})$aryl,
43. $(C_1\text{-}C_6)$alkylene-$(C_4\text{-}C_{10})$heterocyclyl,
44. $(C_1\text{-}C_6)$alkylene-O—$(C_6\text{-}C_{10})$aryl,
45. $(C_1\text{-}C_6)$alkylene-O—$(C_4\text{-}C_{10})$heterocyclyl,
46. O—$(C_6\text{-}C_{10})$aryl,
47. O—$(C_4\text{-}C_{10})$heterocyclyl,
48. O—$(C_1\text{-}C_6)$alkylene-$(C_6\text{-}C_{10})$aryl,
49. O—$(C_1\text{-}C_6)$alkylene-$(C_4\text{-}C_{10})$heterocyclyl, wherein the $(C_6\text{-}C_{10})$aryl and $(C_4\text{-}C_{10})$heterocyclyl groups in residues 40. to 49. are unsubstituted or substituted by 1, 2 or 3 residues independently selected form OH, halogen, NH$_2$, O—$(C_1\text{-}C_6)$alkyl, $(C_1\text{-}C_6)$alkyl, S(O)$_2$—$(C_1\text{-}C_4)$alkyl or $(C_3\text{-}C_{10})$cycloalkyl;

and/or is vicinally substituted by a residue of the formula —O—(CH$_2$)$_n$—O—, wherein n is 1, 2 or 3 and wherein one or more hydrogen atoms may be replaced by halogen atoms; and $R_3$ is H; $(C_1\text{-}C_6)$alkyl or O—$(C_1\text{-}C_6)$alkyl, wherein the $(C_1\text{-}C_6)$alkyl group is unsubstituted or substituted by OH, halogen, NH$_2$, NH$(C_1\text{-}C_6)$alkyl or N[$(C_1\text{-}C_6)$alkyl]$_2$; or $(C_3\text{-}C_{10})$cycloalkyl, wherein $(C_3\text{-}C_{10})$cycloalkyl is unsubstituted or substituted by one or more fluoro atoms;

or a physiologically acceptable salt thereof.

The terms $(C_1\text{-}C_4)$alkyl, $(C_1\text{-}C_6)$alkyl or $(C_1\text{-}C_6)$alkylene are understood as a hydrocarbon residue which can be linear, i.e. straight-chain, or branched and has 1, 2, 3 or 4, or 1, 2, 3, 4, 5 or 6 carbon atoms, respectively. This also applies if an alkyl group occurs as a substituent on another group, for example in an alkoxy group (O-alkyl), a thio group (S-alkyl) or a —O(CH$_2$)$_n$—O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl groups may—if not otherwise stated—be halogenated once or more, i.e. alkyl groups may be fluorinated, i.e. perfluorinated. Examples of halogenated alkyl groups are CF$_3$ and CH$_2$CF$_3$, OCF$_3$, S—CF$_3$, —O—(CF$_2$)$_2$—O—.

Alkenyl are, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

Alkynyl are, for example, ethynyl, 1-propynyl, 2-propynyl (=propargyl) or 2-butynyl.

$(C_3\text{-}C_1)$cycloalkyl groups are cyclic alkyl groups containing 3, 4, 5, 6, 7, 8, 9 or 10 ring carbon atoms like cyclopropyl, cyclobutyl, cyclopentyl, cyclohexyl or cyclooctyl, which can also be substituted and/or unsaturated. Unsaturated cyclic alkyl groups and unsaturated cycloalkyl groups like, for example, tetrahydronaphthyl, cyclopentenyl or cyclohexenyl can be bonded via any carbon atom. The term alkyl as used herein also comprises cycloalkyl-substituted alkyl groups like cyclopropylmethyl-, cyclobutylmethyl-, cyclopentylmethyl-, 1-cyclopropylethyl-, 1-cyclobutylethyl-, 1-cyclopentylethyl-, 2-cyclopropylethyl-, 2-cyclobutylethyl-, 2-cyclopentylethyl-, 3-cyclopropylpropyl-, 3-cyclobutylpropyl-, etc. in which groups the cycloalkyl subgroup as well as acyclic subgroup can be unsaturated and/or substituted. Of course, a cyclic alkyl group has to contain at least three carbon atoms, and an unsaturated alkyl group has to contain at least two carbon atoms. Thus, a group like $(C_1\text{-}C_4)$-alkyl is to be understood as comprising, among others, saturated acyclic $(C_1\text{-}C_4)$-alkyl, $(C_3\text{-}C_4)$-cycloalkyl, cyclopropyl-methyl.

A $(C_6\text{-}C_{10})$aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. Phenyl is a preferred $(C_6\text{-}C_{10})$aryl group.

A $(C_4\text{-}C_{10})$heterocyclyl group means a 4-10 membered mono- or bicyclic ring system which comprises, apart from carbon, one or more heteroatoms such as, for example, e.g. 1, 2, 3 or 4 nitrogen atoms, 1 or 2 oxygen atoms, 1 or 2 sulfur atoms or combinations of different hetero atoms. For example, a $C_6$-heterocyclyl may contain 5 carbon atoms and 1 nitrogen atom as is the case in pyridyl or piperidinyl. The heterocyclyl residues can be bound at any positions, for example on the 1-position, 2-position, 3-position, 4-position, 5-position, 6-position, 7-position or 8-position. Heterocyclyl comprises (1) aromatic $(C_5\text{-}C_{10})$heterocyclyl groups [$(C_5\text{-}C_{10})$heteroaryl groups] or (2) saturated $(C_4\text{-}C_{10})$heterocyclyl groups or (3) mixed aromatic/saturated fused $(C_8\text{-}C_{10})$heterocyclyl groups.

$(C_5\text{-}C_{10})$heteroaryl groups are preferred as $(C_4\text{-}C_{10})$heterocyclyl group.

Suitable $(C_4\text{-}C_{10})$heterocyclyl group include acridinyl, azetidine, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in $(C_4-C_{10})$heterocyclyl residues can occur on free carbon atoms or on nitrogen atoms.

Preferred examples of $(C_4-C_{10})$heterocyclyl residues are 2- or 3-thienyl, 2 or 3-furyl, 1-, 2- or 3-pyrrolyl, 1-, 2-, 4- or 5-imidazolyl, 1-, 3-, 4- or 5-pyrazolyl, 1,2,3-triazol-1-, -4 or -5-yl, 1,2,4-triazol-1-, -3 or -5-yl, 1- or 5-tetrazolyl, 2-, 4- or 5-oxazolyl, 3-, 4- or 5-isoxazolyl, 1,2,3-oxadiazol-4 or -5-yl, 1,2,4-oxadiazol-3 or -5-yl, 1,3,4-oxadiazol-2-yl or -5-yl, 2-, 4- or 5-thiazolyl, 3-, 4- or 5-isothiazolyl, 1,3,4-thiadiazol-2 or -5-yl, 1,2,4-thiadiazol-3 or -5-yl, 1,2,3-thiadiazol-4 or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-chinolyl, 1-, 3-, 4-, 5-, 6-, 7- or 8-isochinolyl, 2-, 4-, 5-, 6-, 7- or 8-chinazolinyl, 3-, 4-, 5-, 6-, 7- or 8-cinnolinyl, 2-, 3-, 5-, 6-, 7- or 8-chinoxalinyl, 1-, 4-, 5-, 6-, 7- or 8-phthalazinyl. Enclosed are also the respective n-oxides, for example 1-oxy-2-, -3 or -4-pyridyl. Particularly preferred $(C_4-C_{10})$heterocyclyl residues are 2- or 3-furyl, 2- or 3-pyrrolyl, 3-, 4- or 5-pyrazolyl, and 2-, 3- or 4-pyridyl.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

"Halogen" means fluoro, chloro, bromo or iodo.

Pyrazolopyridine substitution pattern are numbered according to IUPAC rules:

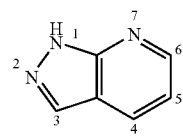

A preferred embodiment of the present invention is a compound of the formula (I) wherein
$R_1$ and $R_3$ are as defined above; and
$R_2$ is phenyl or a $(C_4-C_{10})$heterocyclyl group which are unsubstituted or substituted as defined above.

A further preferred embodiment of the present invention is a compound of the formula (I) wherein
$R_1$ is H;
$R_2$ is phenyl or a $(C_4-C_{10})$heterocyclyl group which are unsubstituted or substituted as defined above; and
$R_3$ is H; $(C_1-C_6)$alkyl which is unsubstituted or substituted by OH, halogen, $NH_2$, $NH(C_1-C_6)$alkyl or $N[(C_1-C_6)$alkyl$]_2$; or a $(C_3-C_{10})$cycloalkyl group which is unsubstituted or substituted by one or more fluoro atoms;
or a physiologically acceptable salt thereof.

A further preferred embodiment of the present invention is a compound of the formula (I) wherein
$R_1$ is H;
$R_2$ is phenyl or a $(C_4-C_{10})$heterocyclyl group which are unsubstituted or substituted as defined above; and
$R_3$ is H;
or a physiologically acceptable salt thereof.

A further preferred embodiment of the present invention is a compound of the formula (I) wherein
$R_1$ is H;
$R_2$ is phenyl or a $(C_5-C_{10})$heteroaryl group which are unsubstituted or substituted as defined above or; and
$R_3$ is H;
or a physiologically acceptable salt thereof.

A further preferred embodiment of the present invention is a compound of the formula (I) wherein
$R_1$ is H;
$R_2$ is a $(C_5-C_{10})$heteroaryl group which is unsubstituted or substituted as defined above; and
$R_3$ is H;
or a physiologically acceptable salt thereof.

Preferred $(C_5-C_{10})$heteroaryl groups as group $R_2$ are benzofuranyl, indolyl, furanyl, pyridyl, pyrrolyl, pyrazolyl, pyrazinyl, pyrimidyl, quinolinyl, thienyl, tetrazolyl, triazolyl, morpholine, pyrrolidinyl, piperazinyl and piperidinyl. Especially preferred are benzofuranyl, indolyl, furanyl, pyridyl, pyrrolyl and pyrazolyl.

More preferred, the $R_2$ group is $(C_5-C_{10})$heteroaryl of the formula (II),

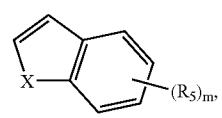

wherein
X is N—$R_4$ or O,
$R_4$ is H, $(C_1-C_4)$alkyl, $(C_2-C_4)$alkenyl, $(C_2-C_4)$alkynyl, $(C_1-C_4)$alkylene-phenyl or $C(O)-(C_1-C_4)$alkyl;
$R_5$ is
1. H,
2. $(C_1-C_4)$alkyl, 3. $(C_2-C_4)$alkenyl,
4. $(C_2-C_4)$alkynyl,
5. $(C_1-C_4)$alkylene-phenyl,
6. $C(O)-(C_1-C_4)$alkyl,
7. COOH,
8. $C(O)O-(C_1-C_4)$alkyl,
9. $C(O)NH_2$,
10. halogen,
11. OH,
12. $O-(C_1-C_4)$alkyl,
13. $O-(C_1-C_4)$alkylene-OH,
14. $O-(C_1-C_4)$alkylene-$NH_2$,
15. $O-(C_1-C_4)$alkylene-$O-(C_1-C_4)$alkyl,
16. $O-(C_1-C_4)$alkylene-phenyl,
17. $O-(C_1-C_4)$alkylene-$(C_5-C_6)$heterocyclyl,
18. $O-(C_1-C_4)$alkylene-C(O)OH,
19. $O-(C_1-C_4)$alkylene-C(O)O-$(C_1-C_6)$alkyl, or
20. $O-(C_1-C_4)$alkylene-C(O)$NH_2$;

m is 1 or 2;
or a furanyl group;
or a pyridyl group;
or a pyrrolyl group which is unsubstituted or substituted by $(C_1-C_6)$alkyl;
or a pyrazolyl group which is unsubstituted or substituted by phenyl.

A further preferred embodiment of the present invention is a compound of the formula (I) wherein
$R_1$ is H; and
$R_2$ is a $(C_5-C_{10})$heteroaryl group of the formula (II), (II)

wherein
X is N—$R_4$,
$R_4$ is H, $CH_3$, $CH(CH_3)_2$, benzyl, $C(=O)CH_3$, $CH_2CH=CH_2$ or $CH_2C\equiv CH$,
$R_5$ is H, $CH_3$, $OCH_3$, COOH, $C(O)OCH_3$, $C(O)NH_2$, O-benzyl, F, Cl, Br, OH, $O(CH_2)_2OH$, $O(CH_2)_2OCH_3$, $O(CH_2)_2NH_2$, $OCH_2C(O)OH$, $OCH_2C(O)NH_2$, $OCH_2C(O)O$-(tert-butyl), m is 1 or 2;
or $R_2$ is a pyridyl group;
or $R_2$ is a furanyl group;
or $R_2$ is a pyrrolyl group of the formula (VII)

(VII)

wherein $R_8$ is H or $(C_1-C_6)$alkyl;
or $R_2$ is a pyrazolyl group of the formula (VIIIa)

(VIIIa)

wherein $R_9$ is phenyl; and
$R_3$ is H:
or a physiologically acceptable salt thereof.

Optically active carbon atoms present in the compounds of the formula (I) can independently of each other have R configuration or S configuration. The compounds of the formula (I) can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula (I) can be present as E isomers or Z isomers (or cis isomers or trans isomers) the invention relates both to pure E isomers and pure Z isomers and to E/Z mixtures in all ratios. The invention also comprises all tautomeric forms of the compounds of the formula (I).

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula (I) can also be obtained by employing stereochemically uniform starting materials or by using stereoselective reactions.

Physiologically acceptable salts of the compounds of formula (I) are nontoxic salts that are physiologically acceptable, in particular pharmaceutically utilizable salts. Such salts of compounds of the formula (I) containing acidic groups, for example a carboxylic group COOH, are for example alkali metal salts or alkaline earth metal salts such as sodium salts, potassium salts, magnesium salts and calcium salts, and also salts with physiologically acceptable quaternary ammonium ions such as tetramethylammonium or tetraethylammonium, and acid addition salts with ammonia and physiologically acceptable organic amines, such as methylamine, dimethylamine, trimethylamine, ethylamine, triethylamine, ethanolamine or tris-(2-hydroxyethyl)-amine. Basic groups contained in the compounds of the formula I, for example amino groups or amidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. The present invention also includes acid addition salts of compounds of the formula (I) which contain, for example, two basic groups, with one or two acid equivalents.

Salts of compounds of the formula (I) can be obtained by customary methods known to those skilled in the art, for example by combining a compound of the formula (I) with an inorganic or organic acid or base in a solvent or diluent, or from other salts by cation exchange or anion exchange. The present invention also includes all salts of the compounds of the formula (I) which, because of low physiologically tolerability, are not directly suitable for use in pharmaceuticals but are suitable, for example, as intermediates for carrying out further chemical modifications of the compounds of the formula (I) or as starting materials for the preparation of physiologically acceptable salts.

The anions of the mentioned acids that may be present in acid addition salts of the compounds of the formula I, are also examples of anions that may be present in the compounds of the formula (I) if they contain one or more positively charged groups like trialkylammonio-substituents, i.e. groups of the formula (alkyl)$_3$N bonded via the positively charged nitrogen atom, representing R, or quaternized ring nitrogen atoms in heterocyclic groups. In general a compound of the formula (I) contains one or more physiologically acceptable anions or anion equivalents as counterions if it contains one or more permanently positively charged groups like trialkylammonio. Compounds of the formula (I) which simultaneously contain a basic group or a positively charged group and an acidic group, for example an amidino group and a carboxy group, can also be present as zwitterions (betaines) which are likewise included in the present invention.

The present invention furthermore includes all solvates of compounds of the formula (I), for example hydrates or adducts with alcohols. The invention also includes derivatives and modifications of the compounds of the formula I, for example prodrugs, protected forms and other physiologically acceptable derivatives including esters and amides of acid groups, as well as active metabolites of the compounds of the formula I.

The compounds of the formula (I), which on account of its chemical structure occurs in enantiomeric forms, can be resolved into the pure enantiomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups.

The compounds of the formula (I) can be isolated either in free form or, in the case of the presence of acidic or basic groups, converting it into physiologically acceptable salts. The preparation of physiologically acceptable salts of compounds of the formula (I) capable of salt formation, including their stereoisomeric forms, is carried out in a manner known per se. With basic reagents such as hydroxides, carbonates, hydrogencarbonates, alkoxides and also ammonia or organic bases, for example trimethyl- or triethylamine, ethanolamine or triethanolamine or alternatively basic amino acids, for example lysine, ornithine or arginine, the carboxylic acids form stable alkali metal, alkaline earth metal or optionally substituted ammonium salts. If the compounds of the formula (I) contain basic groups, stable acid addition salts can also be prepared using strong acids. For this, both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethylsulfonic, acetic, oxalic, tartaric, succinic or trifluoroacetic acid are suitable.

The present invention therefore also relates to the compounds of the formula (I) and/or their physiologically acceptable salts and/or their prodrugs for use as pharmaceuticals (or medicaments), to the use of the compounds of the formula (I) and/or their physiologically acceptable salts and/or their prodrugs for the production of pharmaceuticals for the treatment and prevention of chronic heart failure, hypertension, myocardial ischemia and hepatitis C virus (HCV) infections, and for the prevention of opiate addiction.

The present invention furthermore relates to pharmaceutical preparations (or pharmaceutical compositions) which contain an effective amount of at least one compound of the formula (I) and/or its physiologically acceptable salts and/or its prodrugs and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) physiologically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their physiologically acceptable salts and/or their prodrugs. The amount of the active ingredient of the formula (I) and/or its physiologically acceptable salts and/or its prodrugs in the pharmaceutical preparations normally is from about 0.5 to about 1000 mg, preferably from about 1 to about 500 mg.

In addition to the active ingredients of the formula (I) and/or their physiologically acceptable salts and/or prodrugs and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their physiologically acceptable salts and/or their prodrugs. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physicochemical properties of the compounds and thus allows the selection of such desired compounds. Furthermore, in addition to at least one compound of the formula (I) and/or its physiologically acceptable salts and/or its prodrugs, the pharmaceutical preparations can also contain one or more other therapeutically or prophylactically active ingredients.

As inhibitors of GRK2 the compounds of the formula (I) and their physiologically acceptable salts and their prodrugs are generally suitable for the therapy and prophylaxis of conditions in which the activity of GRK2 or βARK-1 plays a role or has an undesired extent, or which can favorably be influenced by inhibiting GRK2 or βARK-1 or decreasing its activity, or for the prevention, alleviation or cure of which an inhibition of GRK2 or βARK-1 or a decrease in its activity is desired by the physician.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

The compounds of the formula (I) can generally be prepared according to the following scheme:

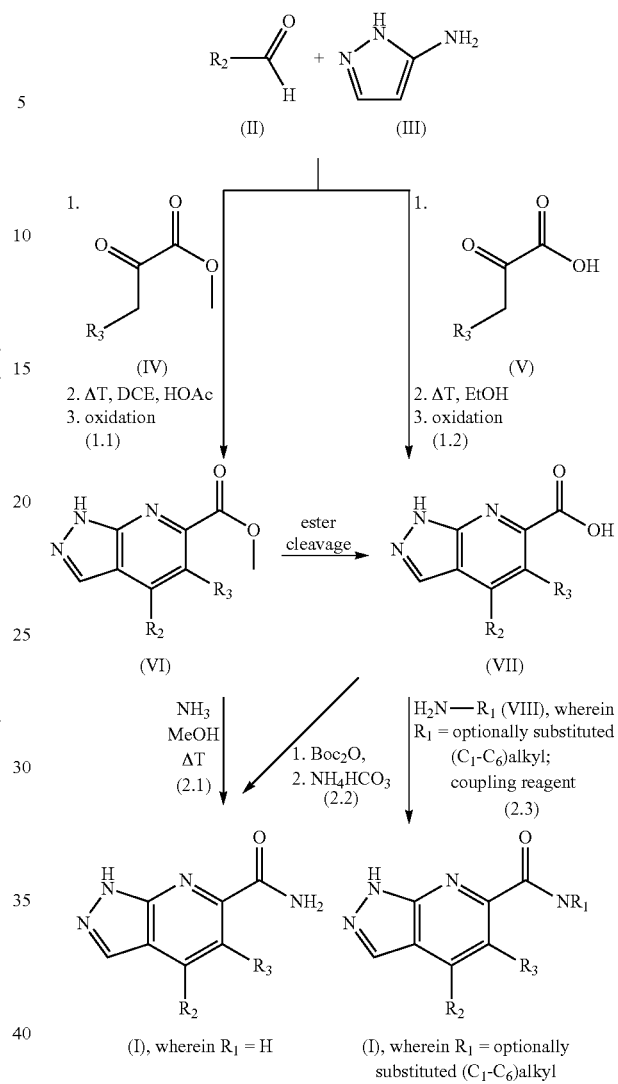

In a first route, $R_2$-aldehyde (II), 3-aminopyrazole (III) and $R_3$-containing methyl pyruvate (IV) are mixed in dichloroethane (DCE) in the presence of an acid, preferably acetic acid, and the mixture is heated to 50-120° C., preferably 60-100° C., and subsequently the reaction mixture is oxidized, preferably by exposure to air whereby the aromatic 1H-Pyrazolo [3,4-b]pyridine system (VI) is formed.

In an alternative route, $R_2$-aldehyde (II), 3-aminopyrazole (III) and $R_3$-containing methyl pyruvic acid (V) are mixed in ethanol and heated to 50-120° C., preferably 60-100° C. Subsequent oxidization, preferably by exposure to air yields the 1H-Pyrazolo[3,4-b]pyridine acid derivative (VII).

Ester cleavage can be achieved by standard methods by e.g. exposing the ester (VI) to a base. Details on methods for the preparation are given in various standard references like, for example, J. March, Advanced Organic Chemistry, 4th ed., John Wiley & Sons, 1992

The respective amides of the formula (I) wherein $R_1$ is hydrogen can be formed by reacting the ester (VI) with a suitable reagent such as e.g. ammonia in methanol or by activating the carboxylic acid derivative (VII) with $Boc_2O$ and treating the resulting tert-butyl ester with $NH_4HCO_3$. In the case a tert-butyl ester is formed at N1 or N2 of the pyrazolopyridine, it can be removed by treatment with TFA. Compounds of the formula (I) wherein $R_1$ is an optionally substituted $(C_1-C_6)$alkyl group can be obtained by coupling the respective $(C_1-C_6)$alkyl-$NH_2$ derivative (VIII) to (VII) in the presence of a standard coupling reagent such as e.g. DIC, dicyclohexyl carbodiimide, EDC, HOBT etc.

Protective groups that may still be present in the products obtained in the coupling reaction are then removed by standard procedures. For example, tert-butyl protecting groups, in particular a tert-butoxycarbonyl group which is a protected form of an amidino group, can be deprotected, i.e. converted into the amidino group, by treatment with trifluoroacetic acid. As already explained, after the coupling reaction also functional groups can be generated from suitable precursor groups. In addition, a conversion into a physiologically acceptable salt or a prodrug of a compound of the formula (I) can then be carried out by known processes.

In general, a reaction mixture containing a final compound of the formula (I) or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

It is understood that modifications that do not substantially affect the activity of the various embodiments of this invention are included within the invention disclosed herein. Accordingly, the following examples are intended to illustrate but not limit the present invention.

Abbreviations

ACN acetonitrile
anh. anhydrous
cpd. compound
DIAD diisopropyl azodicarboxylate
DIC diisopropyl carbodiimide
DMSO dimethyl sulfoxide
$Et_2O$ ethyl ether
MeOH methanol
DMF dimethylformamide
DCM dichloromethane
DCE 1,2-dichloroethane
eq equivalent(s)
HPLC high performance liquid chromatography
r.t. room temperature
THF tetrahydrofuran
TFA trifluoroacetic acid
TLC thin layer chromatography
h hour(s)
$R_t$ retention time Synthesis of Intermediates:

4-Hydroxy-1-methyl-1H-indole-3-carbaldehyde (I-1)

I-1

Step 1

Synthesis of
4-Hydroxy-1-methyl-N-methyl-indole-3-carbaldehyde

To a solution of 4-Benzyloxy-1H-indole-3-carbaldehyde (0.5 g, 2.0 mmol) in anhydrous DMF (8.0 mL) was added methyl iodide (0.148 mL, 2.40 mmol) and potassium carbonate (0.552 g, 4.0 mmol) with vigorous stirring. This solution was then allowed to stir for 36 h at r.t. The solvent was evaporated to give a white solid. The solid was dissolved in ethyl acetate (100 mL), filtered and evaporation of the solvent gave a light grey solid. The solid was triturated with $Et_2O$ to remove residual DMF and filtration gave the product as a fluffy light grey solid 0.40 g (yield: 75%); $^1$H NMR (DMSO $d_6$) 3.85 (s, 3H), 5.35 (s, 2H), 6.9 (dd, 1H), 7.20 (m, 2H), 7.40 (m, 3H), 7.55 (m, 2H), 8.1 (s, 1H), 10.3 (s, 1H); MS m/e 265 ($M^+$).

Step 2

The compound derived from step 1 (0.5 g, 1.9 mmol) was dissolved in DCM (10 mL) and to the solution was added 48% HBr (3.0 mL). This solution was allowed to stir overnight at r.t. The solvent was evaporated to give a dark purple solid. The crude was triturated twice with ethyl acetate, (following subsequent removal of ethyl acetate under reduced pressure). The crude material was purified by column chromatography. Conditions: 0.75 g of crude compound on 25 g of flash grade silica; hexanes/ethyl acetate (50/50). The appropriate fractions were collected and evaporated to give the product as a light green solid 0.275 g (yield: 82%) $^1$H NMR (DMSO $d_6$) 3.85 (s, 3H,), 6.60 (d, 1H), 7.00 (d, 1H), 7.20 (t, 1H), 8.35 (s, 1H), 9.6 (s, 1H), 10.6 (s, 1H); MS m/e 175 ($M^+$).

5-Hydroxy-1-methyl-1H-indole-3-carbaldehyde (I-2)

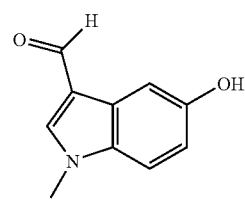

I-2

To a solution of 5-Methoxy-1-methyl-1H-indole-3-carbaldehyde (4.5 g, 23.8 mmol, in 150 ml DCM) was added $BBr_3$ solution (2 M in DCM, 60 ml, 5 eq) at −10° C. with stirring for 5 min. The cooling bath was removed and the reaction mixture was slowly warmed up to r.t. The reaction was monitored by TLC (2% MeOH in DCM) and LCMS (after 3.5 h, no starting material remained). The reaction mixture was then cooled to −10° C., and 16 ml of MeOH were slowly added. The pH of mixture was adjusted to 8 by adding sat. NaHCO$_3$ and/or 4 N NaOH. The organic solvents were removed under reduced pressure and the remaining aqueous mixture was extracted with ethyl acetate (30 ml×5). The organic layers were combined, washed with brine (10 ml×1), dried over Mg$_2$SO$_4$, filtered and dried under reduced pressure to give the title compound as 4.06 g purple powder (yield: 97%) that was used without further purification. LCMS (2-85% ACN/H$_2$O in 7 min): 176.1 (40%). R$_f$ 0.11 (2% MeOH in DCM).

4-[2-(2-pyridyloxy)ethyl]-1-methyl-1H-indole-3-carbaldehyde (I-3)

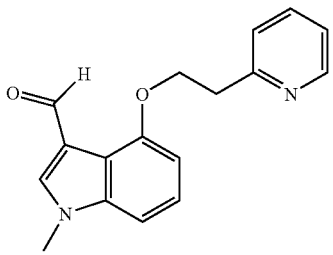

I-3

A solution of 88 mg (0.5 mmol) I-1, 262 mg (1 mmol) PPh$_3$ and 123 mg (1 mmol) dry 2-pyridyl-1-ethanol in 4 ml dry THF, and a solution of 202 mg (1 mmol) DIAD in 1 ml dry THF were cooled to −10° C. and quickly mixed. The temperature was raised to r.t. and stirred for 2 hours. The reaction was monitored by LCMS, evaporated and purified on HPLC (RP YMC-Pack ODS-AM, AM12S05-2520WT, S-5 um, 12 nm, gradient C/water (+0.1% TFA), 10-100% in 20 min, 10 ml/min, UV detection 280 nm). Relevant fractions were lyophilized overnight. LCMS (2 to 85% ACN/H$_2$O): shows MH$^+$ ion m/z=281 (100%). Yield: 90 mg (64%).

5-(N-piperidinoethyloxy)-1-methyl-1H-indole-3-carbaldehyde (I-4)

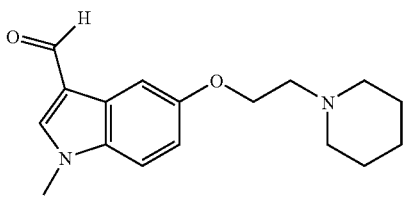

I-4

In analogy to the preparation of I-3, starting from 88 mg (0.5 mmol) of I-2 and 129 mg (1 mmol) of 2-(N-piperidino)-ethanol LCMS shows MH$^+$ ion m/z=287 (100%). HPLC purification provided yield 65 mg (yield: 45%) from HPLC/lyophilization.

3-(3-formyl-1-methyl-1H-indol-5-yloxymethyl)-piperidine-1-carboxylic acid tert-butyl ester (I-5)

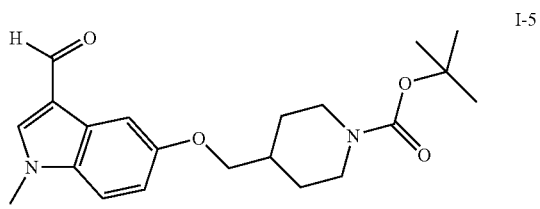

I-5

To a solution of aldehyde I-2 (400 mg, 2.3 mmol) in DMF (10 ml), 3-bromomethyl-piperidine-1-carboxylic acid tert-butyl ester (760 mg, 2.7 mmol) and N'''-tert-butyl-N,N,N',N',N'',N''-hexamethyl-phosphorimidic triamide (1.16 ml, 4.6 mmol) were added. After heating at 100° C. for 6 h, evaporation, and purification by silica gel chromatography (ethyl acetate:hexane 6:4) 350 mg (Yield: 21%) of the title compound could be yielded as solid after evaporation to dryness. LC/MS (M+H)$^+$ 373.

2-(3-Formyl-1-methyl-1H-indol-5-yloxy)-acetamide (I-6)

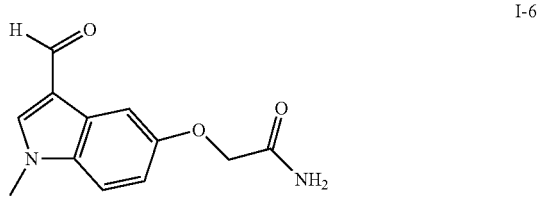

I-6

5-Hydroxy-1-methyl-1H-indole-3-carbaldehyde (I-2) (0.5 g, 2.86 mmol), 2-Bromo-acetamide (0.43 g, 3.1 mmol), and N'''-tert-butyl-N,N,N',N',N'',N''-hexamethyl-phosphorimidic triamide (2.18 mL, 8.6 mmol) were dissolved into anh. DMF (3 mL) in a seal tube. The resulting solution was then sealed and heated at 120° C. (monitored by LCMS). The reaction completed after 3.5 h. The mixture was cooled to room temperature, added 20 mL of water, and 6 N HCl to pH 2-3. The mixture was then extracted with ethyl acetate (20 mL×6). The organic layers were combined, washed with brine (10 mL×2), dried over Mg$_2$SO$_4$, filtered and dried under reduced pressure to give the title compound as 0.5 g orange powder (crude yield: 76%, used without further purification). LCMS (2-85% ACN/H$_2$O in 7 min): M$^+$ 233.1 (100%); 95% purity (at 220 nM).

SYNTHESIS OF EXAMPLES COMPOUNDS

4-{-4-[2-(2-pyridyloxy)ethyl]-1-methyl-1H-indolyl}-7-aza-indazole-6-carboxamide

Example 1

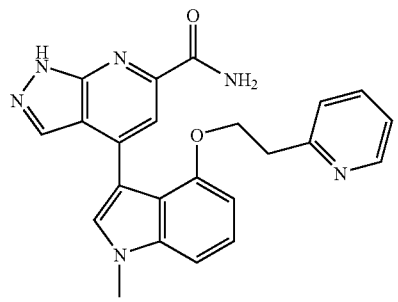

Step 1: Synthesis of 4-{-4-[2-(2-pyridyloxy)ethyl]-1-methyl-1H-indolyl}-6-methoxycarbonyl-7-aza-indazole The solution of 86 mg aldehyde I-3 (0.2 mmol), 18 mg methyl pyruvate (0.2 mmol) and 20 mg of 3-aminopyrazole (0.2 mmol) in DCE (2 ml, 1% acetic acid) was heated in a closed tube at 90° C. for 12 hours and cooled to r.t. The reaction mixture was evaporated under reduced pressure and the residue separated by prep-HPLC (RP YMC-Pack ODS-AM, AM12S05-2520WT, S-5 um, 12 nm, gradient ACN/water (+0.1% TFA), 10-100% in 20 min, 10 ml/min, UV detection 280 nm) Raw yield 32 mg (39%), Step 2

The raw product from step 1 was dissolved into 2 ml of 7 N NH$_3$/MeOH, sealed and heated at 80° C. for 6 h and the solvent was removed under reduced pressure. The residue was purified via prep-HPLC (RP YMC-Pack ODS-AM, AM12S05-2520WT, S-5 um, 12 nm, gradient ACN/water (+0.1% TFA), 10-100% in 20 min, 10 ml/min, UV detection 280 nm) and after lyophilization 1 mg pure product (1% overall yield) were obtained.

$^1$H NMR (600 MHz, DMSO-d$_6$, SM__6425) δ (ppm): 13.63 (bs, 1H), 8.41 (d, J=5.0, 1H), 8.23 (s, 1H), 8.09 (s, 1H), 7.97 (bs, 1H), 7.84 (s, 1H), 7.65 (bs, 1H), 7.52 (m, 1H), 7.23 (m, 1H), 7.19 (dd, J=8.1, 7.1 Hz, 1H), 7.14 (d, J=8.1 Hz, 1H), 6.87 (bd, 1H), 6.71 (d, J=7.1 Hz, 1H), 4.37 (t, 2H), 3.84 (s, 3H), 3.13 (t, 2H).

LCMS (2 to 85% ACN/H$_2$O): shows MH$^+$ ion m/z=413 (100%), R$_t$=3.27.

5-[(N-piperidinoethyloxy)-1-methyl-1H-indol-3-yl]-7-aza-indazole-6-carboxamide

Example 2

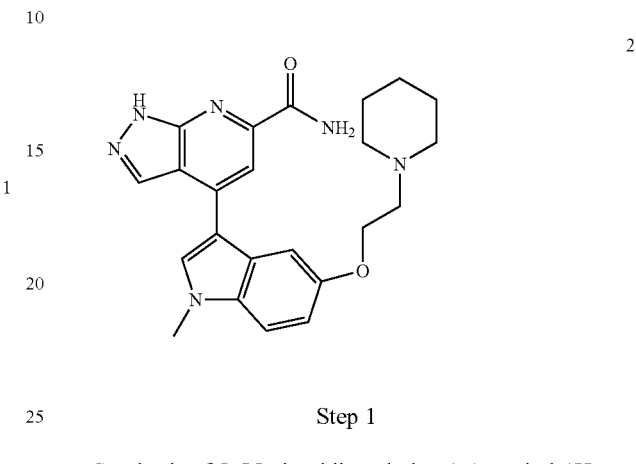

Step 1

Synthesis of 5-(N-piperidinoethyloxy)-1-methyl-1H-indol-3-yl}-6-methoxycarbonyl-7-aza-indazole Preparation in analogy to step 1 of example 1, starting from 65 mg of I-4. Prep-HPLC purification provided 17 mg (yield: 18%) that were used in the next step.

Step 2

Preparation in analogy to step 2 of example 1, starting from 17 mg of the above described compound. Prep-HPLC purification provided 7 mg solid (yield: 7%)

$^1$H NMR (600 MHz, DMSO-d$_6$, SM__6425) δ (ppm): 13.77 (bs, 1H) 8.50 (s, 1H), 8.26 (s, 1H), 8.11 (s, 1H), 8.00 (bs, 1H), 7.71 (bs, 1H), 7.56 (d, J=9.0 Hz, 1H), 7.49 (d, J=2.4 Hz, 1H), 7.07 (dd, J=9.0, 2.4 Hz, 1H), 4.36 (t, 2H), 3.90 (s, 3H), 3.40-3.58 (m, 6H), 1.58-1.75 (m, 6H). (LCMS main peak: 287 mmu). R$_t$=3.31.

4-(1-methyl-5-(piperidin-3-ylmethoxy)-1H-indol-3-yl)-1H-pyrazolo(3,4-b)pyridine-6-carboxylic acid amide Example 3

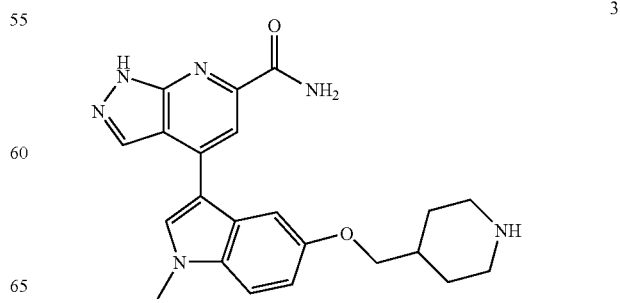

Step 1

Synthesis of 4-(5-(tert-Butoxycarbonyl-piperidine-3-ylmethoxy)-1-methyl-1H-indol-3-yl)-1H-pyrazolo(3,4-b)pyridine-6-carboxylic acid methyl ester)

To a solution of I-5 (350 mg, 946 umol) in DCE (4 ml) were added a solution of 1H-pyrazol-3-ylamine (83 mg, 1 mmol) in DCE (4 ml), a solution of methyl pyruvate (102 mg, 1 mmol) in DCM (4 ml) and acetic acid (500 μl). The solution was stirred at 80° C. for 8 h, evaporated and purified by prep-HPLC (in water with 0.1% TFA using a gradient of 25 to 85% ACN over 9 minutes.) Evaporated to dryness yielded 108 mg (yield: 22%) of the compound as a solid. LC/MS (M+H)$^+$ 520

Step 2

The product obtained from step 1 (200 mg, 385 μmol) was treated with 20 ml 7N ammonia in methanol at 70° C. for 3 h, and evaporated to dryness. The solid was treated with 50% TFA in DCM (6 ml) for 2 h, and evaporated to dryness. Purification by prep-HPLC (in water with 0.1% TFA using a gradient of 5 to 45% ACN over 9 minutes) yielded 40 mg (yield: 48%) of the product as a solid.

$^1$H NMR 600 MHz (DMSO-d$_6$) δ (ppm): 3.90 (1H, m), 3.86 (3H, s), 6.92 (1H, d), 7.41 (1H, s), 7.46 (1H, d), 7.69 (1H, s), 7.99 (1H, m), 8.12 (1H, s), 8.23 (1H (s), 8.51 (1H, s), 13.82 (1H, s); NOE confirmed the assigned structure. LC/MS (M+H)$^+$ 405. R$_f$=3.38.

4-(1-Methyl-1H-indol-3-yl)-1H-indazole-6-carboxylic acid amide

Example 4

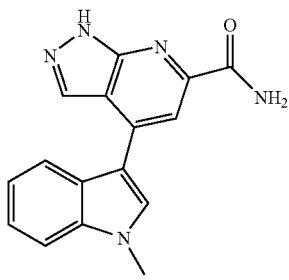

4

Step 1: Synthesis of 4-(1-Methyl-1H-indol-3-yl)-1H-indazole-6-carboxylic acid methyl ester A solution of 1-Methyl-1H-indole-3-carbaldehyde (4 mmol, 0.636 g), methyl pyruvate (4 mmol, 0.361 ml) and 3-aminopyrazole (4 mmol, 0.388 g) in DCE (12 ml, 1% acetic acid) was heated in a sealed tube at 100° C. for 17.5 hours. After that the mixture was cooled down to r.t. and evaporated under reduced pressure.

Subsequently, 10 ml of Et$_2$O was added to the residue and the resulting precipitate was filtered, washed with Et$_2$O (10 ml×2) and dried. The new precipitate from the mother liquid (reduced to 20 mL) was filtered and washed again. After 2 additional cycles, 0.8 g crude product was obtained. The remaining solution was condensed again, 10 ml of MeOH was added and the new precipitate was filtered and washed twice with 1 ml Et$_2$O. After twice repetitions 1.3 g of crude product could be obtained (LCMS: >90% pure@220 nM) and used without further purification in the next step. 70 mg of this crude product was further purified by MS-detected HPLC to afford 21 mg of the pure title compound as red powder. (LCMS main peak: 307 mmu).

Step 2

0.67 g of the above mentioned crude product was dissolved into 7 N NH$_3$/MeOH (25 ml), sealed and heated at 70-80° C. for 18 h. The solvent was removed under reduced pressure. The residue was purified via silica gel chromatography (ethyl acetate/hexane) and 0.2 g of raw product was obtained, and re-purified by MS-triggered HPLC. Finally 7 mg of pure compound was obtained (overall Yield: 10%).

$^1$H NMR (600 MHz, DMSO-d$_6$) δ (ppm): 13.80 (br, 1H), 8.56 (s, 1H), 8.29 (s, 1H), 8.22 (s, 1H), 8.13 (s, 1H), 8.00 (d, J=8.1 Hz, 1H), 7.73 (s, 1H), 7.62 (d, J=8.1 Hz, 1H), 7.34 (dd, J=8.1, 8.1 Hz, 1H), 7.29 (dd, J=8.1, 8.1 Hz, 1H), 3.94 (s, 3H), NOE study (DMSO-d6) confirmed the structure assignment. (LCMS main peak: 292.2 mmu). R$_f$=4.10.

4-(5-Bromo-1H-indol-3-yl)-1H-pyrazolo(3,4-b)pyridine-6-carboxylic acid amide

Example 5

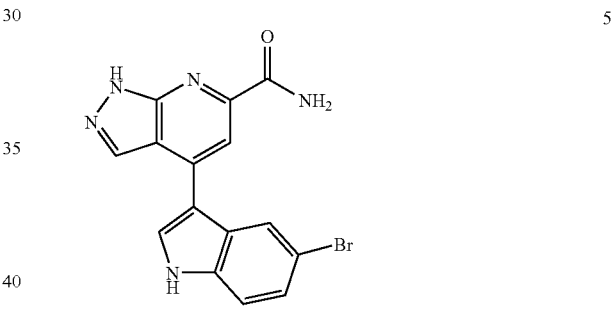

To a solution of 5-bromo-1-H-indole-3-carbaldehyde (1220 mg, 5.4 mmol) in dry ethanol (18 ml) was added a solution of pyruvic acid (475 mg, 5.4 mmol) in dry ethanol (18 ml). The mixture was heated at 80° C. for 1 h, and a solution of 1H-pyrazol-3-ylamine (448 mg, 5.4 mmol) in dry ethanol (18 ml) added. The reaction was heated at 80° C. for 24 h, exposed to air at r.t. for 24 h and evaporated to dryness to yield a raw solid. The solid was dissolved in pyridine/ethyl acetate 1:1 (60 ml) and treated with ammonium bicarbonate (948 mg, 12 mmol) and di-tert-butyl dicarbonate (2.19 g, 12 mmol) for 16 h at r.t. The mixture was then evaporated to dryness, redissolved in ethyl acetate (100 ml), and washed with water/brine (3×), dried (Na$_2$SO$_4$), filtered, and evaporated to dryness. The solid was treated with TFA (50% in DCM) for 2 h at r.t, neutralized carefully with aqueous Na$_2$CO$_3$, extracted with ethyl acetate, dried (Na$_2$SO$_4$), filtered, evaporated and purified by silica gel chromatography (ethyl acetate:hexane 8:2 to pure ethyl acetate gradient). The product was then re-purified by prep-HPLC chromatography in water with 0.1% TFA using a gradient of 15 to 85% ACN over 9 minutes. 3.3 mg (<1% yield) of the product could be obtained as a solid.

$^1$H NMR (600 MHz, DMSO-d$_6$) δ (ppm): 7.37. (d, 1H), 7.51 (d, 1H), 7.63 (s, 1H), 8.01 (s, 1H), 8.09 (s, 1H), 8.29 (s, 1H), 8.48 (s, 1H), 12.12 (s, 1H), 13.80 (s, 1H).

NOE confirmed the assigned structure. LC/MS (M+H)+ 356. $R_f$=4.11.

4-(4-methyl-1H-indol-3-yl)-1H-pyrazolo(3,4-b)pyridine-6-carboxylic acid amide

Example 6

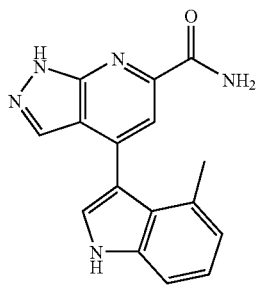

In analogy to the preparation of example 5, 4-methyl-1-H-indole-3-carbaldehyde (477 mg, 3 mmol) was converted yielding 11 mg (yield: 1%) of a solid product.

$^1$H NMR 600 MHz (DMSO-$d_6$) δ ppm: 2.20 (s, 3H), 6.87 (d, 1H), 7.09 (dd, 1H), 7.33 (d, 1H), 7.71 (s, 1H), 7.72 (s, 1H), 7.78 (s, 1H), 8.01 (s, 1H), 8.12 (s, 1H), 11.72 (s, 1H), 13.79 (s, 1H); NOE confirmed the assigned structure. LC/MS (M+H)+ 292. $R_f$=3.86.

4-(4,6-dimethoxy-1-methyl-1H-indol-3-yl)-1H-pyrazolo(3,4-b)pyridine-6-carboxylic acid amide Example 7

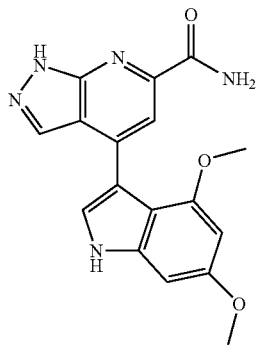

In analogy to the preparation of example 5, 4,6-dimethoxy-1-methyl-1H-indole-3-carbaldehyde (657 mg, 3 mmol) was converted yielding 11 mg (yield: 1%) of a solid product.

LC/MS (M+H)+ 352. $^1$H NMR 600 MHz (DMSO-$d_6$) δ (ppm): 3.71 (s, 3H), 3.79 (s, 3H), 3.82 (s, 3H), 6.32 (s, 1H), 6.68 (s, 1H), 7.59 (s, 1H) 7.74 (s, 1H), 7.90 (s, 1H), 8.11 (s, 1H), 8.23 (s, 1H), 13.66 (s, 1H); NOE confirmed the assigned structure.

4-(5-Carbamoylmethoxy-1-methyl-1H-indol-3-yl)-1H-pyrazolo[3,4-b]pyridine-6-carboxylic acid amide Example 8

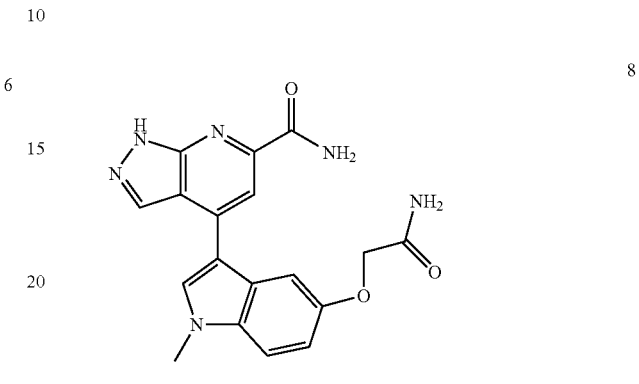

Step 1

Synthesis of 4-(5-Carbamoylmethoxy-1-methyl-1H-indol-3-yl)-1H-pyrazolo[3,4-b]pyridine-6-carboxylic acid methyl ester A mixture of 2-(3-Formyl-1-methyl-1H-indol-5-yloxy)-acetamide (I-6, crude, ~3 mmol, 0.7 g), methyl pyruvate (3 mmol, 0.3 mL), 3-aminopyrazole (3 mmol, 0.29 g) and $Na_2SO_4$ (anh. 0.5 g) in DCE (10 mL) was heated with vigorously stirring in a sealed tube at 100° C. for 17 hours. After that the mixture was cooled down to r.t. and evaporated under reduced pressure.

Subsequently, 12 ml of $H_2O$, 12 ml of DMF and 15 ml of MeOH were added to the residue. The mixture was sonicated for 5 minutes and stirred for additional 10 minutes. The resulting precipitate was filtered, washed with $H_2O$ (2 mL×5) and dried (0.3 g). Both liquid layer and precipitate were analyzed by LCMS, and the precipitate contained most of the expected title compound (M+: 380.2 (100%); LCMS: 90% purity@220 nM). The crude product was used without further purification in the next step.

Step 2

Synthesis of 4-(5-Carbamoylmethoxy-1-methyl-1H-indol-3-yl)-1H-pyrazolo[3,4-b]pyridine-6-carboxylic acid amide The above crude product (0.3 g) was dissolved into 7 N $NH_3$/MeOH (60 ml), sealed and heated at 80° C. overnight. The solvent was removed under reduced pressure. The residue was dissolved into DMSO (5 ml), filtered and purified by MS-triggered HPLC, and gave 0.1 g pure compound (overall Yield: 10%). LCMS (2 to 85% ACN/$H_2O$): 365.2 (100%); 100% purity at 220 nM. $R_f$=3.38.

$^1$H NMR (600 MHz, DMSO-$d_6$) δ (ppm): 13.81 (s, 1H), 8.52 (s, 1H), 8.27 (s, 1H), 8.15 (s, 1H), 8.01 (s, 1H), 7.74 (s, 1H), 7.62 (s, 1H), 7.57 (d, J=9.0 Hz, 1H), 7.50 (d, J=2.3 Hz, 1H), 7.39 (s, 1H), 7.07 (dd, J=2.3, 9.0 Hz, 1H), 4.47 (s, 2H), 3.93 (s, 3H). NOE study (DMSO-d6) confirmed the structure assignment.

The examples in the following Table 1 can be obtained in analogy to the above procedures. MS peaks are given as parent main peaks. A slight modified procedure was applied for Example 55 which was prepared in analogy to example 5 yielding the corresponding carboxylic acid and was subsequently coupled with aminoethanol according to standard amid coupling conditions using DIC as coupling reagent.

The LC/MS system used to obtain the r.t. and MS main peak data was a Waters 2790-ZQ, the column a YMC ProC18 S-5 120A 2×50 mm, the method was 0.1% TFA in water with a gradient of ACN 2-85% over 6.85 minutes. MS ionization method was ESI technique.

TABLE 1

| Example Compound | Structural formula | $R_t$ | MS main peak |
|---|---|---|---|
| 9 | | 3.87 | 239 |
| 10 | | 3.84 | 283 |
| 11 | | 3.85 | 297 |
| 12 | | 3.48 | 229 |

TABLE 1-continued

| Example Compound | Structural formula | $R_t$ | MS main peak |
|---|---|---|---|
| 13 | | 5.02 | 331 |
| 14 | | 4.81 | 345 |
| 15 | | 3.30 | 284 |
| 16 | | 3.21 | 255 |
| 17 | | 4.90 | 345 |

TABLE 1-continued
| Example Compound | Structural formula | $R_t$ | MS main peak |
|---|---|---|---|
| 18 | 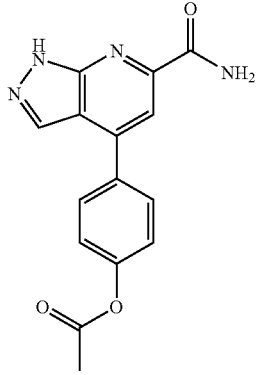 | 3.77 | 297 |
| 19 | 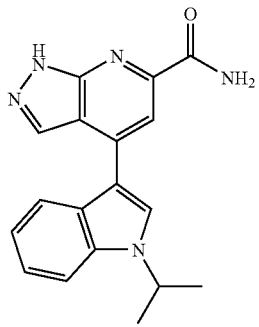 | 4.55 | 320 |
| 20 | 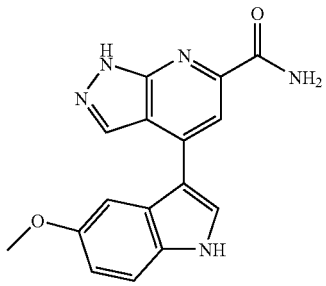 | 3.71 | 308 |
| 21 | 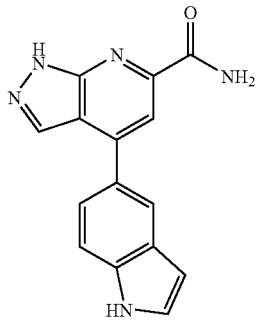 | 3.53 | 278 |

TABLE 1-continued

| Example Compound | Structural formula | $R_t$ | MS main peak |
|---|---|---|---|
| 22 | 1H-pyrazolo[3,4-b]pyridine-6-carboxamide, 4-(4-aminophenyl)-, trifluoroacetic acid salt | 2.40 | 254 |
| 23 | 1H-pyrazolo[3,4-b]pyridine-6-carboxamide, 4-(3-fluoro-4-hydroxyphenyl)- | 3.15 | 273 |
| 24 | 1H-pyrazolo[3,4-b]pyridine-6-carboxamide, 4-(2-chloro-4-hydroxyphenyl)- | 3.36 | 289 |
| 25 | 1H-pyrazolo[3,4-b]pyridine-6-carboxamide, 4-(6-methoxycarbonyl-1H-indol-3-yl)- | 3.36 | 336 |

TABLE 1-continued

| Example Compound | Structural formula | $R_t$ | MS main peak |
|---|---|---|---|
| 26 | | 4.09 | 322 |
| 27 | | 3.22 | 242 |
| 28 | | 3.03 | 296 |
| 29 | | 3.04 | 285 |

TABLE 1-continued
| Example Compound | Structural formula | $R_t$ | MS main peak |
|---|---|---|---|
| 30 | 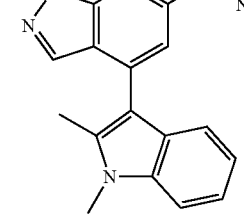 | 4.15 | 306 |
| 31 | 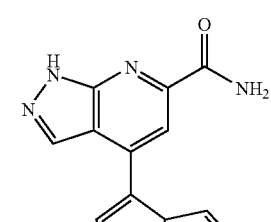 | 3.67 | 278 |
| 32 | 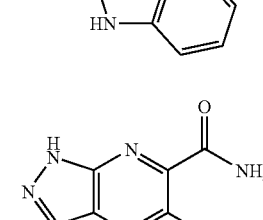 | 4.00 | 306 |
| 33 | 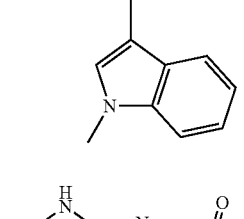 | 3.19 | 305 |
| 34 | 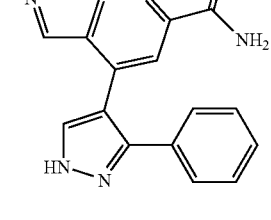 | 3.81 | 299 |

TABLE 1-continued

| Example Compound | Structural formula | $R_t$ | MS main peak |
|---|---|---|---|
| 35 | | 3.80 | 269 |
| 36 | | 3.94 | 299 |
| 37 | | 2.98 | 285 |
| 38 | | 4.56 | 384 |
| 39 | | 4.91 | 368 |

TABLE 1-continued

| Example Compound | Structural formula | $R_t$ | MS main peak |
|---|---|---|---|
| 40 | | 4.57 | 320 |
| 41 | | 3.58 | 278 |
| 42 | | 3.87 | 292 |
| 43 | | 4.04 | 312 |
| 44 | | 3.89 | 292 |

TABLE 1-continued

| Example Compound | Structural formula | $R_t$ | MS main peak |
|---|---|---|---|
| 45 | | 3.89 | 292 |
| 46 | | 4.28 | 384 |
| 47 | | 3.73 | 296 |
| 48 | | 4.23 | 356 |
| 49 | | 4.08 | 322 |

TABLE 1-continued

| Example Compound | Structural formula | $R_t$ | MS main peak |
|---|---|---|---|
| 50 | | 3.68 | 308 |
| 51 | | 4.48 | 318 |
| 52 | | 4.03 | 316 |
| 53 | | 3.01 | 294 |
| 54 | | 2.68 | 229 |

TABLE 1-continued

| Example Compound | Structural formula | $R_t$ | MS main peak |
|---|---|---|---|
| 55 | | 4.03 | 336 |
| 56 | | 2.50 | 254 |
| 57 | | 4.07 | 352 |
| 58 | | 3.63 | 336 |
| 59 | | 3.44 | 405 |

TABLE 1-continued

| Example Compound | Structural formula | $R_t$ | MS main peak |
|---|---|---|---|
| 60 | | 3.36 | 399 |
| 61 | | 3.53 | 352 |
| 62 | | 4.08 | 366 |
| 63 | | 3.19 | 421 |
| 64 | | 3.59 | 421 |

TABLE 1-continued

| Example Compound | Structural formula | $R_t$ | MS main peak |
|---|---|---|---|
| 65 | | 4.01 | 366 |
| 66 | | 3.49 | 405 |
| 67 | | 3.84 | 352 |
| 68 | | 4.12 | 322 |
| 69 | | 3.38 | 399 |

TABLE 1-continued

| Example Compound | Structural formula | $R_t$ | MS main peak |
|---|---|---|---|
| 70 | | 3.18 | 351 |
| 71 | | 3.31 | 399 |
| 72 | | 2.99 | 351 |
| 73 | | 3.56 | 322 |
| 74 | | 3.22 | 391 |

TABLE 1-continued

| Example Compound | Structural formula | R$_t$ | MS main peak |
|---|---|---|---|
| 75 | | 3.62 | 366 |
| 76 | | 4.69 | 422 |
| 77 | | 3.38 | 399 |
| 78 | | 3.41 | 399 |

TABLE 1-continued

| Example Compound | Structural formula | R$_t$ | MS main peak |
|---|---|---|---|
| 79 | [structure: 1H-pyrazolo[3,4-b]pyridine-6-carboxamide linked to 1-methylindole with 5-O-CH₂CH₂-pyridyl ether; trifluoroacetic acid salt] | 3.38 | 413 |
| 80 | [structure: 1H-pyrazolo[3,4-b]pyridine-6-carboxamide linked to 1H-indole-5-carboxamide] | 2.98 | 321 |

Materials and Methods:

The assay determines phosphorylation of biotinylated bovine tubulin dimers (250 nM; TEBU-BIO, # T333) coated to 384 well StreptaWell plates by 100 nM GRK2 which has been pre-incubated with inhibitor cpd. for 30 minutes at room temperature in assay buffer (20 mM Tris-HCl pH 7.4, 2 mM EDTA) containing 2.25% DMSO. The phosphorylation reaction was started by adding tubulin, MgCl$_2$ (10 mM), ATP (3 µM), [γ-$^{33}$P]-ATP (0.4 µCi/40 µl) to the preincubated GRK2/compound complex. Then the assay mix was incubated for 30 min at room temperature before the kinase reaction was stopped adding 0.8% BSA, 0.8% Triton X 100, 80 mM EDTA and 400 µM ATP) followed by an 2-24 h incubation at +4° C. Due to the high energy of the γ-particles free $^{33}$P-ATP is removed by a washing step (3× with 100 µl 1×PBS pH 8.0) using a Tecan Power washer 384 to reduce background activity. Bound $^{33}$P is determined by scintillation counting (60 µl scintillator, Ultimagold MV, 30 sec mix) using a Microbeta-counter (delay time 30 min).

TABLE 2

| Example | IC50 (βARK-1), [µM] |
|---|---|
| 3 | 0.7 |
| 4 | 0.27 |
| 8 | 0.02 |
| 16 | 2.1 |
| 64 | 1.3 |

The invention claimed is:

1. A compound of the formula (I)

(I)

wherein
R$_1$ is
H or
(C$_1$-C$_6$)alkyl, wherein the (C$_1$-C$_6$)alkyl group is unsubstituted or substituted by one or more OH, halogen or NH$_2$ groups;
R$_2$ is
phenyl,
(C$_3$-C$_{10}$)cycloalkyl group or
(C$_4$-C$_{10}$)heterocyclyl group,
each of which are unsubstituted or substituted independently by 1, 2 or 3 residues selected from
1) (C$_1$-C$_6$)alkyl,
2) (C$_2$-C$_6$)alkenyl,
3) (C$_2$-C$_6$)alkynyl,
4) (C$_1$-C$_6$)alkylene-COOH,
5) (C$_1$-C$_6$)alkylene-C(O)O—(C$_1$-C$_6$)alkyl,
6) (C$_1$-C$_6$)alkylene-C(O)NH$_2$,
7) (C$_1$-C$_6$)alkylene-C(O)NH—(C$_1$-C$_6$)alkyl,
8) (C$_1$-C$_6$)alkylene-O—(C$_1$-C$_6$)alkyl,
9) (C$_1$-C$_6$)alkylene-OH,
10) (C$_1$-C$_6$)alkylene-NH$_2$,
11) (C$_1$-C$_6$)alkylene-NH—(C$_1$-C$_6$)alkyl,
12) (C$_1$-C$_6$)alkylene-N[(C$_1$-C$_6$)alkyl]$_2$,
13) CN,
14) COOH,
15) C(O)O—(C$_1$-C$_6$)alkyl, 16) C(O)NH$_2$,
17) C(O)NH—(C$_1$-C$_6$)alkyl,
18) C(O)N[(C$_1$-C$_6$)alkyl]$_2$,
19) C(O)—(C$_1$-C$_6$)alkyl,
20) halogen,
21) NH$_2$,
22) NH(C$_1$-C$_6$)alkyl,
23) N[(C$_1$-C$_6$)alkyl]$_2$,
24) NH—C(O)—(C$_1$-C$_6$)alkyl,
25) OH,
26) O—(C$_1$-C$_6$)alkyl,
27) O—(C$_2$-C$_6$)alkenyl,
28) O—(C$_2$-C$_6$)alkynyl,
29) O—(C$_1$-C$_6$)alkylene-C(O)OH,
30) O—(C$_1$-C$_6$)alkylene-C(O)O—(C$_1$-C$_6$)alkyl,
31) O—(C$_1$-C$_6$)alkylene-C(O)NH$_2$,
32) O—(C$_1$-C$_6$)alkylene-C(O)NH—(C$_1$-C$_6$)alkyl,
33) O—(C$_1$-C$_6$)alkylene-OH,
34) O—(C$_1$-C$_6$)alkylene-O—(C$_1$-C$_6$)alkyl,
35) O—(C$_1$-C$_6$)alkylene-NH$_2$,
36) O—(C$_1$-C$_6$)alkylene-NH—(C$_1$-C$_6$)alkyl,
37) O—C(O)—(C$_1$-C$_6$)alkyl,
38) S—(C$_1$-C$_6$)alkyl,
39) S(O)$_2$—(C$_1$-C$_4$)alkyl,
40) (C$_6$-C$_{10}$)aryl,
41) (C$_4$-C$_{10}$)heterocyclyl,
42) (C$_1$-C$_6$)alkylene-(C$_6$-C$_{10}$)aryl,
43) (C$_1$-C$_6$)alkylene-(C$_4$-C$_{10}$)heterocyclyl,
44) (C$_1$-C$_6$)alkylene-O—(C$_6$-C$_{10}$)aryl,
45) (C$_1$-C$_6$)alkylene-O—(C$_4$-C$_{10}$)heterocyclyl,
46) O—(C$_6$-C$_{10}$)aryl,
47) O—(C$_4$-C$_{10}$)heterocyclyl,
48) O—(C$_1$-C$_6$)alkylene-(C$_6$-C$_{10}$)aryl, and
49) O—(C$_1$-C$_6$)alkylene-(C$_4$-C$_{10}$)heterocyclyl,
wherein the (C$_6$-C$_{10}$)aryl and (C$_4$-C$_{10}$)heterocyclyl in residues 40) to 49) are each unsubstituted or substituted independently by 1, 2 or 3 residues selected from OH, halogen, NH$_2$, O—(C$_1$-C$_6$)alkyl, (C$_1$-C$_6$)alkyl, S(O)$_2$—(C$_1$-C$_4$)alkyl or (C$_3$-C$_{10}$)cycloalkyl;
and/or is vicinally substituted by a residue of the formula —O—(CH$_2$)$_n$—O—, wherein n is 1, 2 or 3 and wherein one or more hydrogen atoms may be replaced by halogen atoms; and
R$_3$ is
H,
(C$_1$-C$_6$)alkyl or O—(C$_1$-C$_6$)alkyl, wherein the (C$_1$-C$_6$) alkyl is unsubstituted or substituted by OH, halogen, NH$_2$, NH(C$_1$-C$_6$)alkyl or N[(C$_1$-C$_6$)alkyl]$_2$, or
(C$_3$-C$_{10}$)cycloalkyl, which is unsubstituted or substituted by one or more fluoro atoms;
or a physiologically acceptable salt thereof.

2. The compound according to claim 1, wherein R$_2$ is phenyl or (C$_4$-C$_{10}$)heterocyclyl.

3. The compound according to claim 2, wherein
R$_1$ is H; and
R$_3$ is H,
(C$_1$-C$_6$)alkyl, which is unsubstituted or substituted by OH, halogen, NH$_2$, NH(C$_1$-C$_6$)alkyl or N[(C$_1$-C$_6$)alkyl]$_2$, or
(C$_3$-C$_{10}$)cycloalkyl, which is unsubstituted or substituted by one or more fluoro atoms.

4. The compound according to claim 2 wherein
R$_1$ is H; and
R$_3$ is H.

5. The compound according to claim 2 wherein
R$_1$ is H;
R$_2$ is phenyl or
(C$_4$-C$_{10}$)heterocyclyl, which is (C$_5$-C$_{10}$)heteroaryl; and
R$_3$ is H.

6. The compound according to claim 1 wherein R$_2$ is (C$_4$-C$_{10}$)heterocyclyl, which is (C$_5$-C$_{10}$)heteroaryl.

7. The compound according to claim 1 wherein R$_2$ is (C$_4$-C$_{10}$)heterocyclyl, which is (C$_5$-C$_{10}$)heteroaryl selected from the group of benzofuranyl, indolyl, furanyl, pyridyl, pyrrolyl, pyrazolyl, pyrazinyl, pyrimidyl, quinolinyl, thienyl, tetrazolyl, and triazolyl.

8. A compound according to claim 1 wherein
R$_2$ is (C$_4$-C$_{10}$)heterocyclyl, which is (C$_5$-C$_{10}$)heteroaryl that is a group of the formula (II),

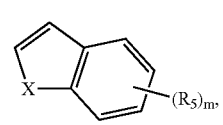

(II)

wherein
X is N—R$_4$ or O,
R$_4$ is H, (C$_1$-C$_4$)alkyl, (C$_2$-C$_4$)alkenyl, (C$_2$-C$_4$)alkynyl, (C$_1$-C$_4$)alkylene-phenyl or C(O)—(C$_1$-C$_4$)alkyl;
R$_5$ is
H,
(C$_1$-C$_4$)alkyl,
(C$_2$-C$_4$)alkenyl,
(C$_2$-C$_4$)alkynyl,
(C$_1$-C$_4$)alkylene-phenyl,
C(O)—(C$_1$-C$_4$)alkyl,
COOH,
C(O)O—(C$_1$-C$_4$)alkyl,
C(O)NH$_2$,
halogen,
OH,
O—(C$_1$-C$_4$)alkyl,
O—(C$_1$-C$_4$)alkylene-OH,
O—(C$_1$-C$_4$)alkylene-NH$_2$,
O—(C$_1$-C$_4$)alkylene-O—(C$_1$-C$_4$)alkyl,
O—(C$_1$-C$_4$)alkylene-phenyl,
O—(C$_1$-C$_4$)alkylene-(C$_5$-C$_6$)heterocyclyl,
O—(C$_1$-C$_4$)alkylene-C(O)OH,
O—(C$_1$-C$_4$)alkylene-C(O)O—(C$_1$-C$_6$)alkyl, or
O—(C$_1$-C$_4$)alkylene-C(O)NH$_2$, and
m is 1 or 2,
furanyl,
pyridyl,
pyrrolyl which is unsubstituted or substituted by (C$_1$-C$_6$) alkyl, or
pyrazolyl which is unsubstituted or substituted by phenyl.

9. The compound according to claim 1 wherein
R$_1$ is H; and
R$_2$ is (C$_5$-C$_{10}$)heteroaryl group of the formula (II),

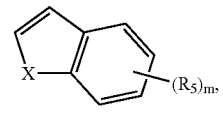

(II)

wherein
X is N—R$_4$,
R$_4$ is H, CH$_3$, CH(CH$_3$)$_2$, benzyl, C(=O)CH$_3$, CH$_2$CH=CH$_2$ or CH$_2$C≡CH, R$_5$ is H, CH$_3$, OCH$_3$, COOH, C(O)OCH$_3$, C(O)NH$_2$, O-benzyl, F, Cl, Br, OH, O(CH$_2$)$_2$OH, O(CH$_2$)$_2$OCH$_3$, O(CH$_2$)$_2$NH$_2$, OCH$_2$C(O)OH, OCH$_2$C(O)NH$_2$, OCH$_2$C(O)O-(tert-butyl),

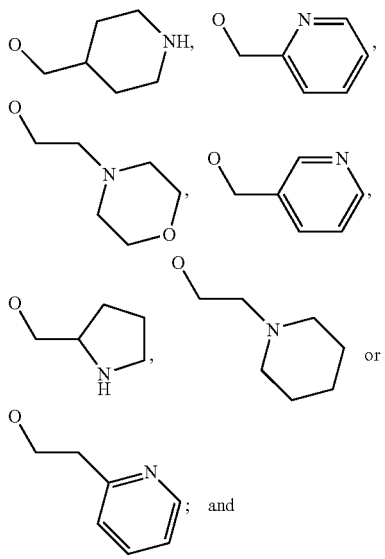

m is 1 or 2,
pyridyl;
furanyl;
pyrrolyl of the formula (VII)

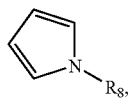
(VII)

wherein R$_8$ is H or (C$_1$-C$_6$)alkyl, or
pyrazolyl of the formula (VIIIa)

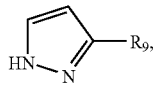
(VIIIa)

wherein R$_9$ is phenyl; and
R$_3$ is H.

10. Method for the preparation of a compound of a compound of the formula (I) as claimed in claim 1, comprising either
a) mixing the compounds of the following formulae (II), (III) and (IV)

(II)

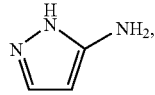
(III)

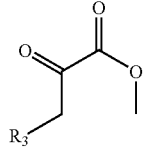
(IV)

in dichloroethane in the presence of an acid, heating the mixture to 50-120° C. and subsequently oxidizing the mixture to yield 1H-Pyrazolo[3,4-b]pyridine system (VI)

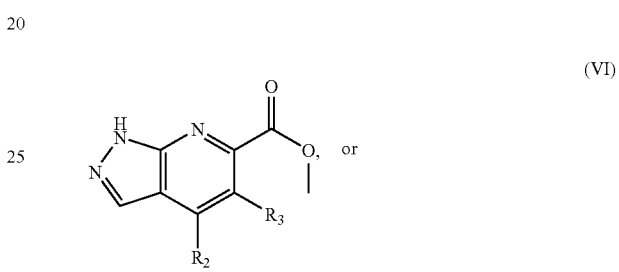
(VI)

reacting compound (VI) with ammonia in methanol to yield a compound of the formula (I) wherein R$_1$ is hydrogen.

11. The method of claim 10 wherein the oxidizing is effected by exposure to air.

12. Method for the preparation of a compound of a compound of the formula (I) as claimed in claim 1, comprising either
a) mixing compounds of the following formulae (II), (III) and (V) in ethanol,

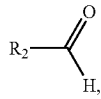
(II)

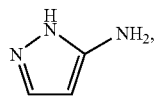
(III)

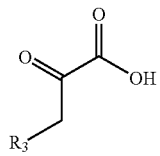
(V)

heating the mixture to 50-120° C., subsequently oxidizing the mixture to yield the 1H-Pyrazolo[3,4-b]pyridine acid derivative (VII)

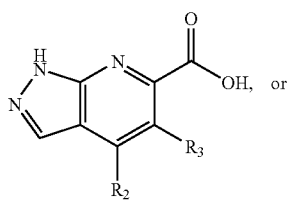 (VII)

b) exposing the compound (VI) according to claim 10 to a base to yield the compound (VII), and then alternatively
a) activating the compound (VII) with $Boc_2O$ and subsequently treating with $NH_4HCO_3$ to yield a compound of the formula (I) wherein $R_1$ is hydrogen, or b) reacting compound (VII) with dicyclohexyl-carbodiimide, EDC or HOBT and $R_1$—$NH_2$ derivative (VIII) to yield a compound of the formula (I) wherein $R_1$ is an optionally substituted ($C_1$-$C_6$)alkyl group.

13. A pharmaceutical composition comprising an effective amount at least one compound of the formula (I) according to claim 1 or a physiologically acceptable salt thereof and physiologically tolerated excipients and carriers, and, where appropriate, further additives and/or other active ingredients.

14. A method of inhibiting Adrenergic receptor in a patient comprising administering to the patient at least one compound according to claim 1, or a pharmaceutically acceptable salt thereof.

* * * * *